United States Patent
Shibuya et al.

(10) Patent No.: US 7,884,106 B2
(45) Date of Patent: Feb. 8, 2011

(54) METHOD OF STABILIZING LIPID-RICH PLAQUE AND METHOD OF PREVENTING RUPTURE THEREOF

(75) Inventors: Kimiyuki Shibuya, Tokorozawa (JP); Hideyuki Kobayashi, Saitama (JP); Yasunobu Yoshinaka, Iruma (JP)

(73) Assignee: Kowa Company, Ltd., Aichi (JP)

( * ) Notice: Subject to any disclaimer, the term of this patent is extended or adjusted under 35 U.S.C. 154(b) by 18 days.

(21) Appl. No.: 10/569,642

(22) PCT Filed: Aug. 19, 2004

(86) PCT No.: PCT/JP2004/011935

§ 371 (c)(1), (2), (4) Date: Feb. 27, 2006

(87) PCT Pub. No.: WO2005/020996

PCT Pub. Date: Mar. 10, 2005

(65) Prior Publication Data

US 2007/0004749 A1   Jan. 4, 2007

(51) Int. Cl.
*A61K 31/497* (2006.01)
(52) U.S. Cl. .................... 514/253.09; 514/253
(58) Field of Classification Search ............ 514/253.09
See application file for complete search history.

(56) References Cited

U.S. PATENT DOCUMENTS

| | | | |
|---|---|---|---|
| 4,346,227 A | 8/1982 | Terahara et al. | |
| 4,444,784 A | 4/1984 | Hoffman et al. | |
| 5,011,930 A | 4/1991 | Fujikawa et al. | |
| 5,177,080 A | 1/1993 | Angerbauer et al. | |
| 5,491,172 A | 2/1996 | Lee et al. | |
| 5,856,336 A | 1/1999 | Fujikawa et al. | |
| 6,969,711 B2 | 11/2005 | Shibuya et al. | |
| 6,974,806 B2 | 12/2005 | Terashita et al. | |
| 6,998,486 B2 | 2/2006 | Shibuya et al. | |
| 2003/0232809 A1 * | 12/2003 | Terashita et al. | 514/224.2 |
| 2004/0038987 A1 | 2/2004 | Shibuya et al. | |
| 2006/0046992 A1 | 3/2006 | Aoki et al. | |
| 2009/0275595 A1 | 11/2009 | Kobayashi et al. | |

FOREIGN PATENT DOCUMENTS

| | | |
|---|---|---|
| CA | 2290744 | 12/1998 |
| EP | 0987254 A1 * | 5/1998 |
| EP | 0 987 254 A1 | 3/2000 |
| EP | 1 314 423 A1 | 5/2003 |
| GB | 2 280 675 A | 2/1995 |
| JP | 1-279866 A | 11/1980 |
| JP | 11-515025 A | 12/1999 |
| JP | 2002-255808 A | 9/2002 |
| WO | WO94/26702 A1 | 11/1994 |
| WO | 97 16184 A1 | 5/1997 |
| WO | WO98/54153 | 12/1998 |
| WO | 01 22962 A1 | 4/2001 |
| WO | WO 01/34127 A1 | 5/2001 |
| WO | 02 20009 A1 | 3/2002 |
| WO | WO03/057675 A1 | 7/2003 |
| WO | 2004-076441 A1 | 9/2004 |

OTHER PUBLICATIONS

Falk et al., Coronary Plaque Disruption, Circulation (1995) 92:657-671, printed pp. 1-47.*
Falk et al., Circulation; Coronary Plaque Disruption, Circulation. 1995; 92:657-671, printed pp. 1-47, especially p. 7 and 16.*
Libby et al. (Macrophages and atherosclerotic plaque stability, Curr Opin Lipidol. Oct. 1996; 7(5):330-5).*
International Search Report of International Application PCT/JP2004/011935 mailed Nov. 30, 2004.
Franklin H. Epstein, M.D., "Mechanisms of Disease, the Pathogenesis of Coronary Artery Disease and the Acute Coronary Syndromes", The New England Journal of Medicine, Jan. 23, 1992, vol. 326, No. 4, pp. 242-250.
Masanori Aikawa et al., "Lipid Lowering Reduces Proteolytic and Prothrombotic Potential in Rabbit Atheroma", Ann. N.Y. Acad. Sci., 902, 2000, pp. 140-152.
Brian R Krause et al., "Emerging therapies in atherosclerosis", Exp. Opin. Invest. Drugs, 1995, 4(5), pp. 353-387.
Bruce D. Roth, "ACAT inhibitors: evolution from cholesterol-absorption inhibitors to antiatherosclerotic agents", Drug Discovery Today, vol. 3., No. 1, Jan. 1998, pp. 19-25.

(Continued)

*Primary Examiner*—Sreeni Padmanabhan
*Assistant Examiner*—Timothy E Betton
(74) *Attorney, Agent, or Firm*—Westerman, Hattori, Daniels & Adrian, LLP

(57) ABSTRACT

A method of stabilizing lipid-rich plaques and method of preventing the rupture thereof, characterized in that an effective amount of 2-[4-[2-(benzimidazol-2-ylthio)ethyl]piperazin-1-yl]-N-[2,4-bis(methylthio)-6-methyl-3-pyridyl]acetamide, its acid adduct salt or a hydrate thereof is administered to patients with lipid-rich plaques. Prevention of plaque rupture and stabilization of plaques can be attained by reducing the occupancy of macrophages in lipid-rich plaques being unstable and tending to rupture among plaques being a lesion from a seat of atherosclerosis and simultaneously increasing the occupancy of collagen therein.

10 Claims, 5 Drawing Sheets

OTHER PUBLICATIONS

Mark D. Rekhter, "Hypercholesterolemia Causes Mechanical Weakening of Rabbit Atheroma", Circulation Research, 2000, pp. 101-108.

Y. Nakashima, et al. "ApoE-Deficient Mice Develop Lesions of All Phases of Atherosclerosis Throughout the Arterial Tree", Arteriosclerosis, Thrombosis, and Vascular Biology, Journal of the American Heart Association; vol. 14, No. 1, Jan. 1994, pp. 133-140.

Florian Bea, et al. "Simvastatin Promotes Atherosclerotic Plaque Stability in ApoE-Deficient Mice Independently of Lipid Lowering" Atherosclerosis and Lipoproteins, Arterioscler Thromb Vasc Biol., Nov. 2002, pp. 1832-1837.

Milita Crisby, MD, et al. "Pravastatin Treatment Increases Collagen Content and Decreases Lipis Content, Inflammation, Metalloproteinases, and Cell Death in Human Carotid Plaques Implications for Plaque Stabilization", Pravastatin Alters Carotid Plaque Composition, Circulation Feb. 20, 2001, pp. 926-933.

Chinese Office Action dated Jul. 6, 2007; Application No. 200480024894.2.

Canadian Office Action dated Nov. 5, 2007, issued in corresponding Canadian Patent Application No. 2,535,920.

Bocan et al., "Comparison of CI-976, an ACAT Inhibitor, and Selected Lipid-Lowering Agents for Antiatherosclerotic Activity in Iliac-Femoral and Thoracic Aortic Lesions. A biochemical, morphological, and morphometric evaluation", Arterioscler Thromb Vasc Biol., vol. 11, No. 6, Nov./Dec. 1991, pp. 1830-1843.

Giovannoni et al., "Selective ACAT Inhibitors as Promising Antihyperlipidemic, Antiatherosclerotic and Anti-Alzheimer Drugs", Mini Reviews in Medicinal Chemistry, 2003, vol. 3, No. 6, pp. 576-584.

Bocan et al., "The ACAT Inhibitor Avasimibe Reduces Macrophages and Matrix Metalloproteinase Expression in Atherosclerotic Lesions of Hypercholesterolemic Rabbits", Arterioscler Thromb Vasc Biol., Jan. 2000, pp. 70-79.

Libby et al., "Stabilization of atherosclerotic plaques: New mechanisms and clinical targets", Nature Medicine, vol. 8, No. 11, Nov. 2002, pp. 1257-1262.

Russian Office Action dated Jul. 1, 2008 (mailing date), issued in corresponding Russian Patent Application No. 2006110035/14(010896).

Shevchenko, "Cardiology", Moscow, 2006, Moscow Information Agency MIA, p. 305).

Gemma Llaverias et al., "Avasimibe and atorvastatin synergistically reduce cholesteryl ester content in THP-1 macrophages", European Journal of Pharmacology, vol. 451, No. 1, (2002), pp. 11-17.

International Search Report of PCT/JP2005/023088, dated of mailing Feb. 7, 2006.

Notification Concerning Transmittal of Copy of International Preliminary Report on Patentability (Form PCT/IB/326) of International Application No. PCT/JP2005/023088 mailed Jun. 21, 2007 with Forms PCT/IB1373 and PCT/ISA/237.

Dr. Terje R. Pedersen, "Randomised trial of cholesterol lowering in 4444 patients with coronary heart disease: the Scandinavian Simvastatin Survival Study (4S)", Lancet, Nov. 19, 1994, vol. 344, pp. 1383-1389.

Antonio M. Gotto, Jr., MD, DPhil, "Cholesterol Management in Theory and Practice", Circulation, Dec. 16, 1997, vol. 96, No. 12, pp. 4424-4430.

James Shepherd, M.D. et al., "Prevention of Coronary Heart Disease with Pravastatin in Men with hypercholesterolemia", The New England Journal of Medicine, Nov. 16, 1995, vol. 333, No. 20, pp. 1301-1307.

Frank M. Sacks, M.D. et al., "The Effect of Pravastatin on Coronary Events after Myocardinal Infarction in Patients with Average Cholesterol Levels", The New England Journal of Medicine, Oct. 3, 1996, vol. 336, No. 14, pp. 1001-1009.

Dr. Andrew Tonkin et al., "Prevention of Cardiovascular Events and Death with Pravastatin in Patients with Coronary heart disease and a broad Range of Initial Cholesterol Levels", The New England Journal of Medicine, Nov. 5, 1998, vol. 339, pp. 1349-1357.

Masanori Aikawa et al. "Lipid Lowering by Diet Reduces Matrix Metalloproteinase Activity and increases Collagen Content of Rabbit Atheroma: A Potential Mechanism of Lesion Stabilization", Circulation, 1998, vol. 97, pp. 2433-2444.

Segrest, Jere P. et al.; "Pathogenesis of atherosclerosis"; Current Opinion in Cardiology, GB, vol. 9, No. 4, 1194, pp. 404-410. XP008126660.

Delsing, Dianne J. M. et al.; "Acyl-CoA:Cholesterol Acyltransferase Inhibitor Avasimibe Reduces Atherosclerosis in Addition to its Cholesterol-Lowering Effect in ApoE*3-Leiden Mice"; Circulation, vol. 1003, No. 13, Apr. 3, 2001, pp. 1778-1786. XP002599626.

Supplementary European Search Report dated Sep. 21, 2010, issued in corresponding European Patent Application No. 04 77 1896.0.

* cited by examiner

METHOD OF STABILIZING LIPID-RICH PLAQUE AND METHOD OF PREVENTING RUPTURE THEREOF

TECHNICAL FIELD

The present invention relates to a method of stabilizing lipid-rich plaques in the atherosclerotic lesions and a method of preventing the rupture thereof. More specifically, the present invention relates to a method of stabilizing lipid-rich plaques and a method of preventing the rupture thereof by suppressing accumulation of macrophages and increasing collagen in the plaque lesions by administering an effective amount of 2-[4-[2-(benzimidazol-2-ylthio)ethyl]piperazin-1-yl]-N-[2,4-bis(methylthio)-6-methyl-3-pyridyl]acetamide, an acid salt thereof or a hydrate thereof.

BACKGROUND ART

Recently, arteriosclerotic diseases are increasing due to changes of life-style as a result of improvement in living standards such as ingestion of a high-calorie diet and a high-cholesterol diet, lack of exercise, obesity, stress caused by social complexities, aging society, and the like. Risk factors of arteriosclerotic diseases can be classified into smoking, obesity, hypertension, hyperuricemia, diabetes mellitus, hyperlipidemia, and the like. Among them, hyperlipidemia such as hypertriglyceridemia, hypo-HDL (HDL: high-density lipoprotein) and hyper-LDL (LDL: low-density lipoprotein) draws increasing attention, and particularly lowering hyper-cholesterol level is placed emphasis as an object for the pharmacotherapy, and various treatments have been performed. In particular, a drug (statin drug), which can achieve significant results in treatment of hypercholesterolemia, is the drug inhibiting HMG-CoA (HMG-CoA: 3-hydroxy-3-methylglutaryl-coenzyme A) reductase, a rate-limiting enzyme of cholesterol biosynthesis, can be mentioned. Cholesterol lowering therapy using statin shows successful results specifically in various arteriosclerotic diseases, for example myocardial infarction and cerebral infarction, caused by hyperlipidemia. With regard to coronary arterial diseases including acute myocardial infarction, results of multicenter epidemiological surveys such as 4S (Scandinavian Simvastatin Survival Study) and WOS (COPS) (West of Scotland Coronary Prevention Study) were reported, and effectiveness of simvastatin therapy has been proven in an improvement of survival rate for five years. However, even if the statin drug represented by simvastatin (Patent Reference 1) and pravastatin (Patent Reference 2) is said to be effective, improvement rate for rate of crisis of coronary disease event is no more than about 30%, and is not satisfactory condition in the medical field. As a mechanism for development of drug efficacy with the statin, it is known that as a result of generating the inhibition of cholesterol biosynthesis in vivo and simultaneously occurring increased expression of LDL receptors accompanied by lowering cholesterol level in the liver, the increased LDL receptors promote incorporation of blood LDL and cause to decrease total cholesterol level in plasma. Consequently, there is a problem that complete lowering LDL cholesterol cannot be expected in patients with homozygote and heterozygote who are deficient of LDL receptor such as familial hypercholesterolemia. It is known that combined medication of fibrate and statin to the patient with hypertriglyceridemia causes rhabdomyolysis, and in case of cerivastatin (Patent Reference 3), severe side effect caused by such the medication resulted to discontinuation of sales. Considering such background, drugs, which do not exhibit anti-arteriosclerotic action coupled with lowering total cholesterol level in plasma but exhibit direct action to arteriosclerosis lesion, is attractive and to be expected.

Plaques, which are the primary focus of atherosclerosis, consist of the lipid core filled with cholesterol and ester thereof and the fibrous material called extracellular matrix. Among the plaques, lipid-rich plaques, which are predominantly made up of lipid and inflammatory cells such as macrophage and covered with thin fibrous membrane, are called "unstable plaques". It is easy to rupture, and when the plaques rupture, contents of the plaques are exposed to the blood flow to promote thrombogenesis. As a result, acute coronary syndrome (ACS) such as unstable angina, acute myocardial infarction and ischemic sudden death will occur (Non-Patent Reference 1). Actually, it is known that as a result of examination of culprit lesion in the cases of death caused by ACS, about 75% of the cases were due to thrombogenesis accompanied by rupture of the plaques (Non-Patent Reference 2). Focusing attention on stenotic rate of blood vessel, i.e. plaque size, the culprit lesion of myocardial infarction was found mainly to be the region of blood vessel with the stenotic rate below 50% (Non-Patent Reference 2). This fact suggests that causes for plaque rupture are not the size of the plaque size but the quality of the plaque.

Involvement of matrix metalloprotease (MMP) secreted by the large amount of accumulated macrophage is considered to be direct cause for the plaque rupture, and MMP may degrade the fibrous collagen to thin and weaken the fibrous film. Further, the macrophage is reported to stimulate the thrombogenesis at the ruptured region through expression of the tissue factor (Non-Patent Reference 3).

Consequently, prevention of the rupture of "unstable plaques" may be important in countermeasure for ACS. For that purpose, methods including inhibition of the function or the accumulation of macrophages, or inhibition of the degradation of the fibrous collagen or strengthening the fibrous cap by increasing the collagen content may be considered. In conclusion for prevention and treatment of acute coronary syndrome, although regression of the plaques accompanied by reducing total cholesterol level in plasma may be effective, instead drugs for inhibiting accumulation of the macrophage and increasing the collagen, as a result, stabilizing lipid-rich plaques may be more preferable.

Considering these situations, acyl-CoA: cholesterol O-acyltransferase (ACAT) inhibitor has been drawn attention as cholesterol lowering drug having different mechanism of action to the statin.

Although there are large numbers of reports indicating regression of plaques by using ACAT inhibitor, significant decrease in plasma total cholesterol level is accompanied in any cases. Consequently, it is unknown whether direct regression of plaques could be achieved or not, and as a result, there may be discrepancy in interpretation of data (Non-Patent References 4 and 5).

However, recently, several ACAT inhibitors, which show regression effect of plaques without affecting the plasma total cholesterol level, have reported. For example, JP-A-2002-255808 (Patent Reference 4) discloses ACAT inhibitor as a plaque regressing agent. WO 01/034127 (Patent Reference 5) discloses ACAT inhibitor, which leads to decrease accumulation of macrophage and expression of MMP in the plaques. However, although the plaque reducing activities were indicated in these reports, they fail to mention increase or decrease of the collagen, one of important factor contributing to the stability of the plaques (Non-Patent Reference 6). Although the compound (avasimibe, hereinafter designated as CI-1011) examined therein exhibits plaque regressing activity, no finding such as increase of collagen and stability is indicated.

As obvious from above, ACAT inhibitor, which is different from conventional ACAT inhibitors, and independently reduces the occupation rate of macrophages in the plaques without affecting the plasma total cholesterol level and has action to increase the occupation rate of collagen as well as preventing rupture of the plaques without leading to diffuse macrophages even if they are ruptured. Such ACAT inhibition has not been known.

Patent Reference 1: U.S. Pat. No. 4,444,784.
Patent Reference 2: U.S. Pat. No. 4,346,227.
Patent Reference 3: U.S. Pat. No. 5,177,080.
Patent Reference 4: JP-A-2002-255808.
Patent Reference 5: WO 01-034127.
Non-Patent Reference 1: N. Engl. J. Med. 326(4): 242-50, 1992.
Non-Patent Reference 2: Circulation 92(3): 657-71, 1995.
Non-Patent Reference 3: Ann. N.Y. Acad. Sci. 902:140-52, 2000.
Non-Patent Reference 4: Exp. Opin. Invest. Drugs 4: 353-387, 1995.
Non-Patent Reference 5: Drug Discovery Today 3: 19-25, 1998.
Non-Patent Reference 6: Circ. Res. 86: 101-8, 2000.

DISCLOSURE OF THE INVENTION

Problem to be Solved by the Invention

In consideration of the above, the inventors have, after extensively studied, found that 2-[4-[2-(benzimidazol-2-ylthio)ethyl]piperazin-1-yl]-N-[2,4-bis(methylthio)-6-methyl-3-pyridyl]acetamide (hereinafter designated as compound 1), an acid salt thereof or a hydrate thereof disclosed in Example 32 of WO 98/054153 could reduce the occupation rate of macrophages in the plaques and increase the occupation rate of collagen without affecting significant changes of the plasma total cholesterol level, namely suggesting stability activity of lipid-rich plaques, and completed the present invention. ACAT inhibitor, which has selective activity for macrophage, of the compound 1 and production method thereof are disclosed in WO 98/054153, the description of which has been incorporated herein by reference. Use of the compound disclosed therein is treatment of hypercholesterolemia and atherosclerosis. Although it describes inhibitor for (selective) foam cell formation of macrophage, no description on the plaque stabilizing activity is found.

Means to Solve the Problems

The present invention provides a method of stabilizing lipid-rich plaques in atherosclerotic lesions and method of preventing the rupture thereof, characterized in that an effective amount of the compound 1, an acid salt thereof or a hydrate thereof is administered to a patient with lipid-rich plaques. Further, the present invention provides a stabilizing agent for lipid-rich plaques and a preventing agent for rupture thereof comprising the compound 1, an acid salt thereof or a hydrate thereof as an active ingredient. Further the present invention provides a pharmaceutical composition having activities for stabilizing lipid-rich plaques comprising the compound 1, an acid salt or a hydrate thereof, and a pharmaceutically acceptable carrier thereof. Still further the present invention provides use of the compound 1, an acid salt thereof or a hydrate thereof for production of the stabilizing agent for lipid-rich plaques and the preventing agent for rupture thereof.

The present invention provides a method of preventing thrombogenesis accompanied to the rupture of lipid-rich plaques, characterized in that an effective amount of the compound 1, an acid salt thereof or a hydrate thereof is administered to a patient with lipid-rich plaques. Further, the present invention provides an agent having activity for preventing thrombogenesis accompanied to the rupture of lipid-rich plaques comprising the compound 1, an acid salt thereof or a hydrate thereof as an active ingredient. Further the present invention provides a pharmaceutical composition having activity for preventing thrombogenesis accompanied to the rupture of lipid-rich plaques comprising the compound 1, an acid salt thereof or a hydrate thereof, and a pharmaceutically acceptable carrier thereof. Still further the present invention provides use of the compound 1, an acid salt thereof or a hydrate thereof for production of the pharmaceutical preparation for prevention of thrombogenesis accompanied to the rupture of lipid-rich plaques.

The present invention provides a method of preventing and/or treating acute coronary syndrome, characterized in that an effective amount of the compound 1, an acid salt thereof or a hydrate thereof is administered to a patient with lipid-rich plaques. Further, the present invention provides an agent for preventing and/or treating acute coronary syndrome comprising the compound 1, an acid salt thereof or a hydrate thereof as an active ingredient. Further the present invention provides a pharmaceutical composition having activities for preventing and/or treating acute coronary syndrome comprising the compound 1, an acid salt thereof or a hydrate thereof, and a pharmaceutically acceptable carrier thereof. Still further the present invention provides use of the compound 1, an acid salt thereof or a hydrate thereof for production of the pharmaceutical preparation for preventing and/or treating acute coronary syndrome.

The present invention provides a method of preventing and/or treating acute myocardial infarction, characterized in that an effective amount of the compound 1, an acid salt thereof or a hydrate thereof is administered to a patient with lipid-rich plaques. Further, the present invention provides an agent for preventing and/or treating acute myocardial infarction comprising the compound 1, an acid salt thereof or a hydrate thereof as an active ingredient. Further the present invention provides a pharmaceutical composition having activities for preventing and/or treating acute myocardial infarction comprising the compound 1, an acid salt thereof or a hydrate thereof, and a pharmaceutically acceptable carrier thereof. Still further the present invention provides use of the compound 1, an acid salt thereof or a hydrate thereof for production of the pharmaceutical preparation for preventing and/or treating acute myocardial infarction.

The present invention provides a method of preventing and/or treating unstable angina, characterized in that an effective amount of the compound 1, an acid salt thereof or a hydrate thereof is administered to a patient with lipid-rich plaques. Further, the present invention provides an agent for preventing and/or treating unstable angina comprising the compound 1, an acid salt thereof or a hydrate thereof as an active ingredient. Further the present invention provides a pharmaceutical composition having activities for preventing and/or treating unstable angina comprising the compound 1, an acid salt thereof or a hydrate thereof, and a pharmaceutically acceptable carrier thereof. Still further the present invention provides use of the compound 1, an acid salt thereof or a hydrate thereof for production of the pharmaceutical preparation for preventing and/or treating unstable angina.

The present invention provides a method of preventing and/or treating peripheral artery obstruction, characterized in that an effective amount of the compound 1, an acid salt thereof or a hydrate thereof is administered to a patient with lipid-rich plaques. Further, the present invention provides an agent for preventing and/or treating peripheral artery obstruction comprising the compound 1, an acid salt thereof or a hydrate thereof as an active ingredient. Further the present invention provides a pharmaceutical composition having activities for preventing and/or treating peripheral artery obstruction comprising the compound 1, an acid salt thereof or a hydrate thereof, and a pharmaceutically acceptable carrier thereof. Still further the present invention provides use of the compound 1, an acid salt thereof or a hydrate thereof for production of the pharmaceutical preparation for preventing and/or treating peripheral artery obstruction.

BEST MODE FOR CARRYING OUT THE INVENTION

The present inventors have studied effects of administration of ACAT inhibitor on the plasma total cholesterol level and the vascular lesion by using ApoE knockout mice.

Figure 1:
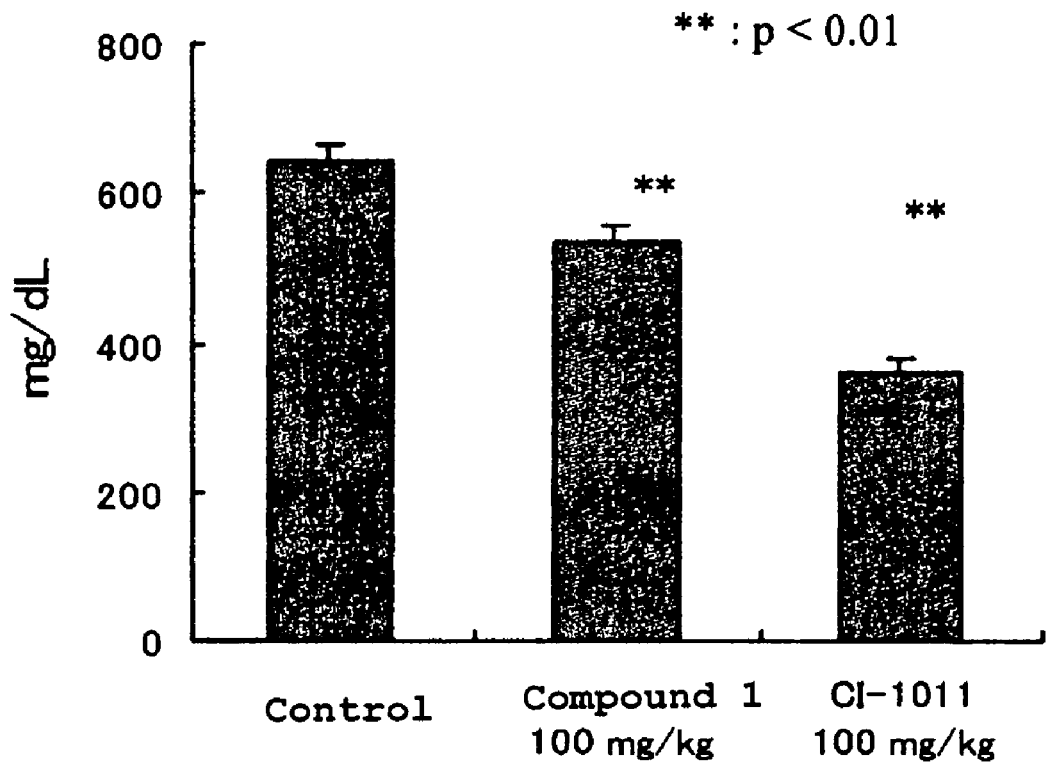
FIG. 1 shows plasma total cholesterol level, when the compound 1 (100 mg/kg), CI-1011 (100 mg/kg) or vehicle was administered orally, twice a day for 12 weeks in male ApoE knockout mice.

In the study examining the effect on the plasma total cholesterol level, the compound 1 (100 mg/kg), CI-1011 (100 mg/kg) or vehicle were administered orally, twice a day for 12 weeks in male ApoE knockout mice, and the plasma total cholesterol level was measured. Results are shown in FIG. 1. The axis of ordinate in FIG. 1 indicates the plasma total cholesterol level (mg/dl). As shown in FIG. 1, significantly decreased plasma levels of total cholesterol were shown in any of the compound 1 administered group and the CI-1011 administered group as compared with the control group. It was found that the degree of the decreased value was small in the compound 1, but was remarkable in the CI-1011.

In parallel with the evaluation of the plasma lipids, the aortic sinus was surgically removed and embedded in paraffin, then serial sections were prepared, thereafter Victoria blue-hematoxylin-eosin staining, Azan staining, macrophage immunohistochemical staining (anti-CD11b antibody) and Sirius Red staining were performed.

Figure 2:
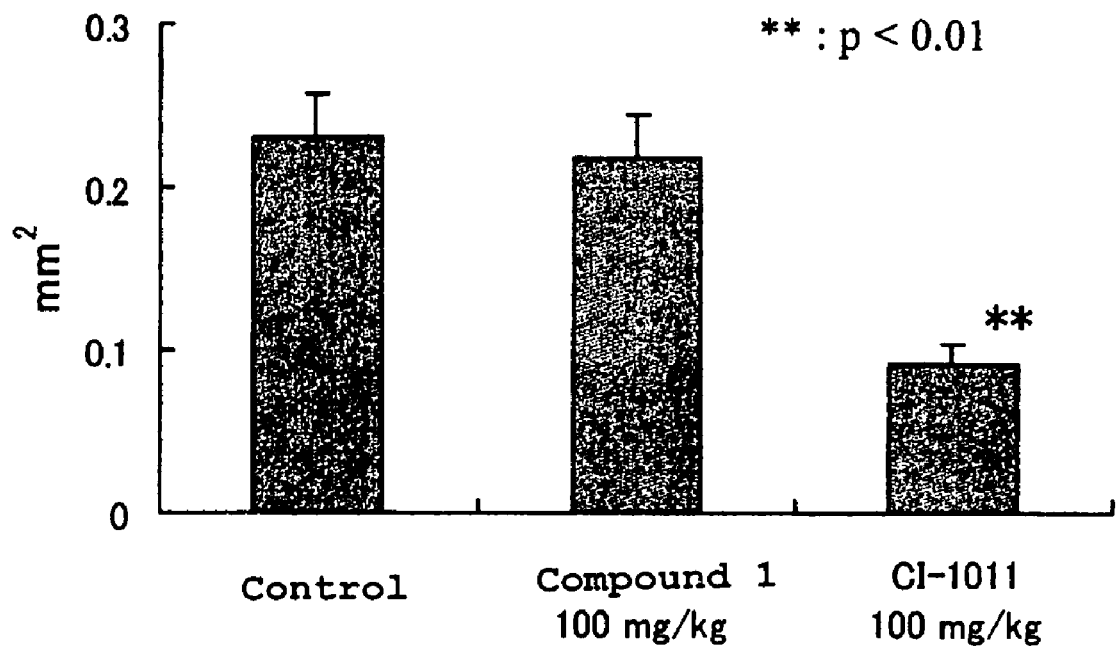
FIG. 2 shows a cross-sectional area of the plaques measured by staining the specimens of surgically removed aortic sinus with Victoria blue-HE (HE: hematoxylin-eosin), after the compound 1 (100 mg/kg), CI-1011 (100 mg/kg) or vehicle were administered orally, twice a day for 12 weeks in male ApoE knockout mice.

Using the specimens of Victoria blue-hematoxylin-eosin staining, the internal elastic layer was analyzed by observation of optical microscope. The specified cross-sectional area of the plaques in the specimens is shown in FIG. 2. The axis of ordinate in FIG. 2 indicates the cross-sectional area of the plaques ($mm^2$). As shown in FIG. 2, the area was almost not changed in the compound 1 administered group, but the cross-sectional area of the plaques was significantly decreased in the CI-1011 administered group as compared with the control group.

Figure 3:
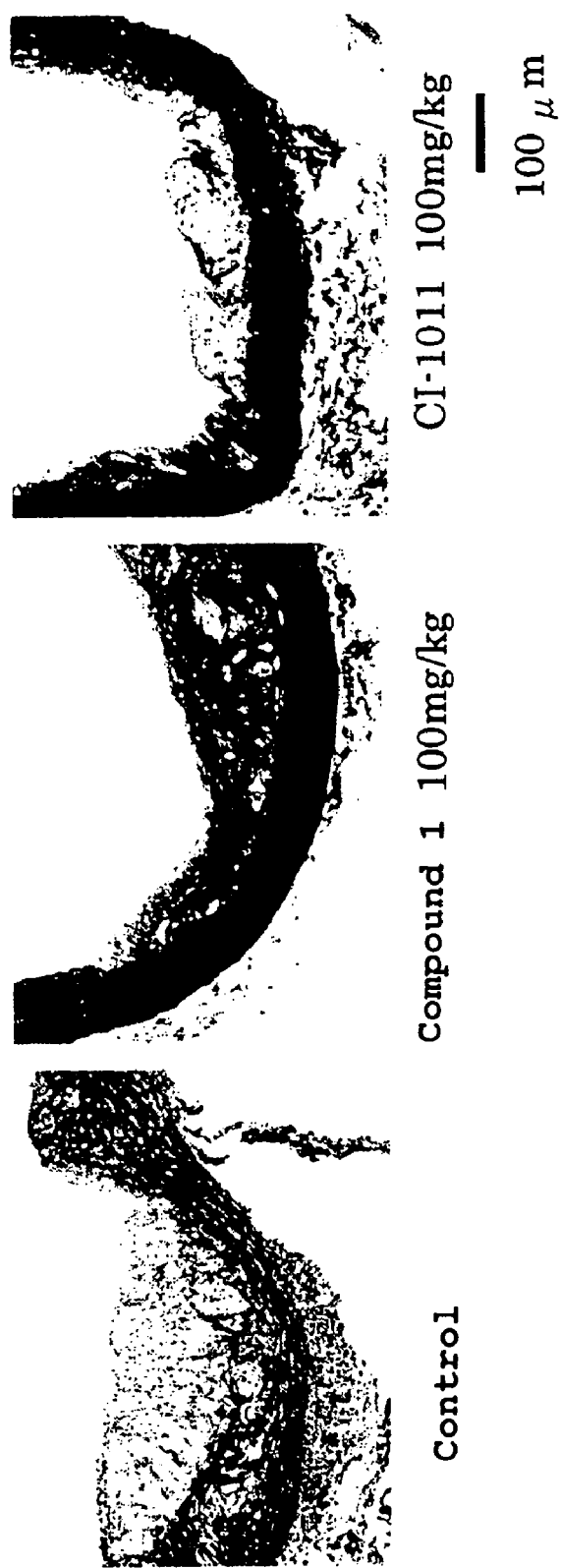
FIG. 3 shows photographs showing results of Azan staining of the specimens of surgically removed aortic sinus, after the compound 1 (100 mg/kg), CI-1011 (100 mg/kg) or vehicle were administered orally, twice a day for 12 weeks in male ApoE knockout mice.

Results of Azan staining are shown in FIG. 3. As shown in FIG. 3, in the control group, the surface layer side of the inner membrane consists largely of the pale red stained foamy macrophages, and the blue stained extracellular matrix was slightly observed in the deep layer. Large numbers of white defective acicular areas called cholesterol craft were observed in the plaque. Contrary, although the cross-sectional area of the plaque in the compound 1 administered group was not so different as compared with the control group, the plaque consisted of small area of cellular components and large numbers of surrounding extracellular matrix. In CI-1011 administered group, although the cross-sectional area of the plaque was slightly smaller as compared with that of the control group, the plaque consisted of mostly red stained macrophage and the blue stained extracellular matrix was scanty.

Figure 4:
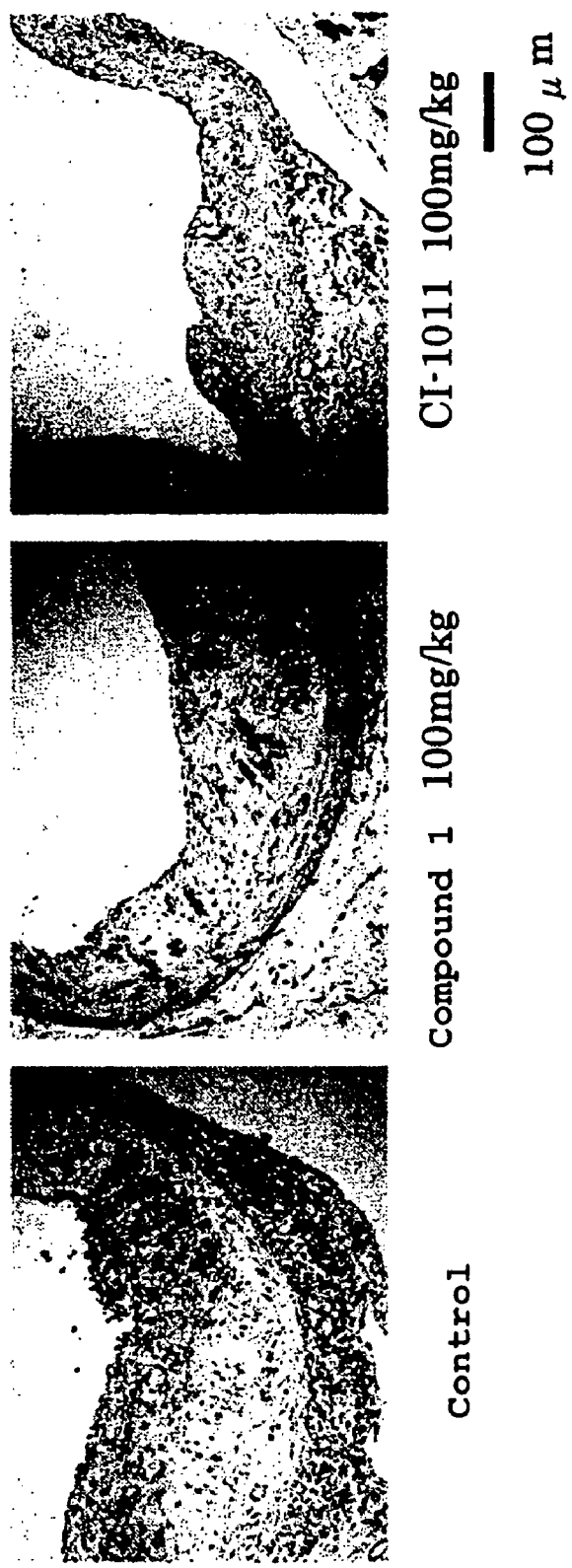
FIG. 4 shows photographs showing results of immunohistochemical staining of macrophages in the specimens of surgically removed aortic sinus, after the compound 1 (100 mg/kg), CI-1011 (100 mg/kg) or vehicle were administered orally, twice a day for 12 weeks in male ApoE knockout mice.

Results of the macrophage immunohistochemical staining are shown in FIG. 4. As shown in FIG. 4, although the macrophages were abundantly observed specifically in the surface layer side of the plaque in the control group, the macrophages were occasionally observed in the compound 1 administered group. Contrary, the macrophages were observed abundantly in whole plaque in the CI-1011 administered group.

Figure 5:
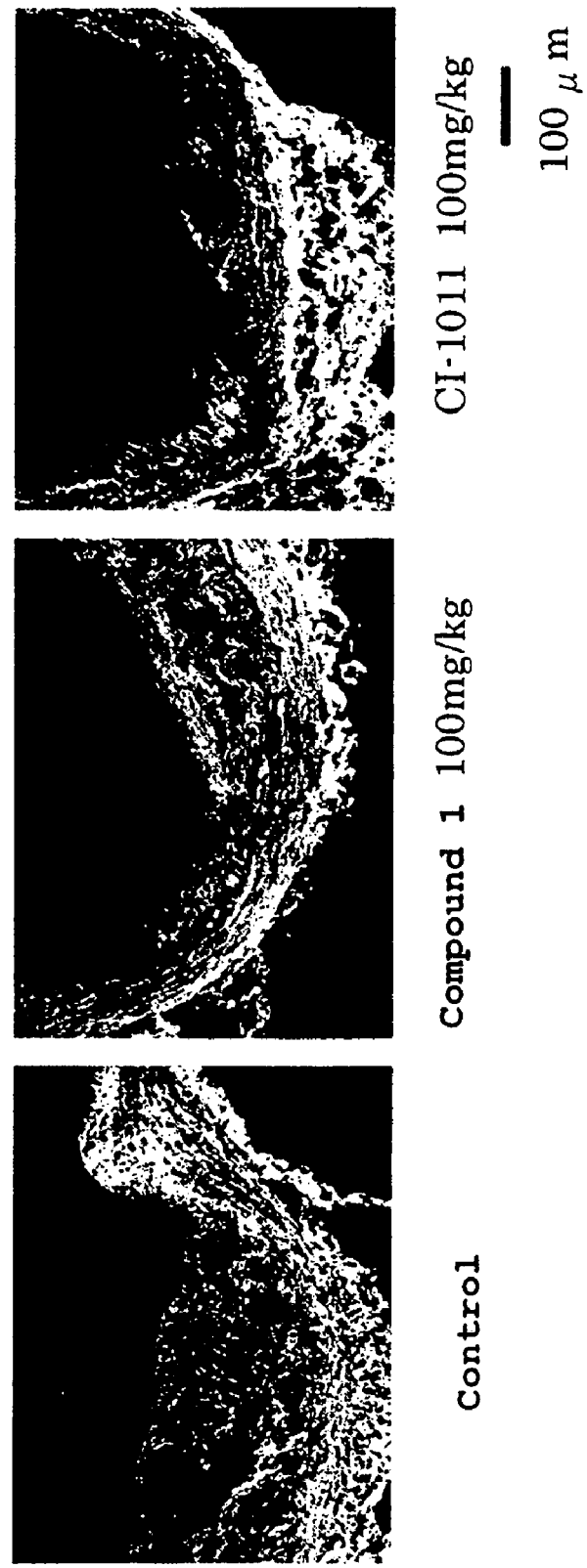
FIG. 5 shows photographs showing results of Sirius Red staining of the specimens of surgically removed aortic sinus, after the compound 1 (100 mg/kg), CI-1011 (100 mg/kg) or vehicle were administered orally, twice a day for 12 weeks in male ApoE knockout mice.

Results of Sirius Red staining are shown in FIG. 5. As shown in FIG. 5, compactly-arranged collagen fibers were observed all over the plaque in the compound 1 administered group as compared with the control group. However, in CI-1011 administered group, smaller numbers of collagen fibers were observed as compared with the control group.

Figure 6:
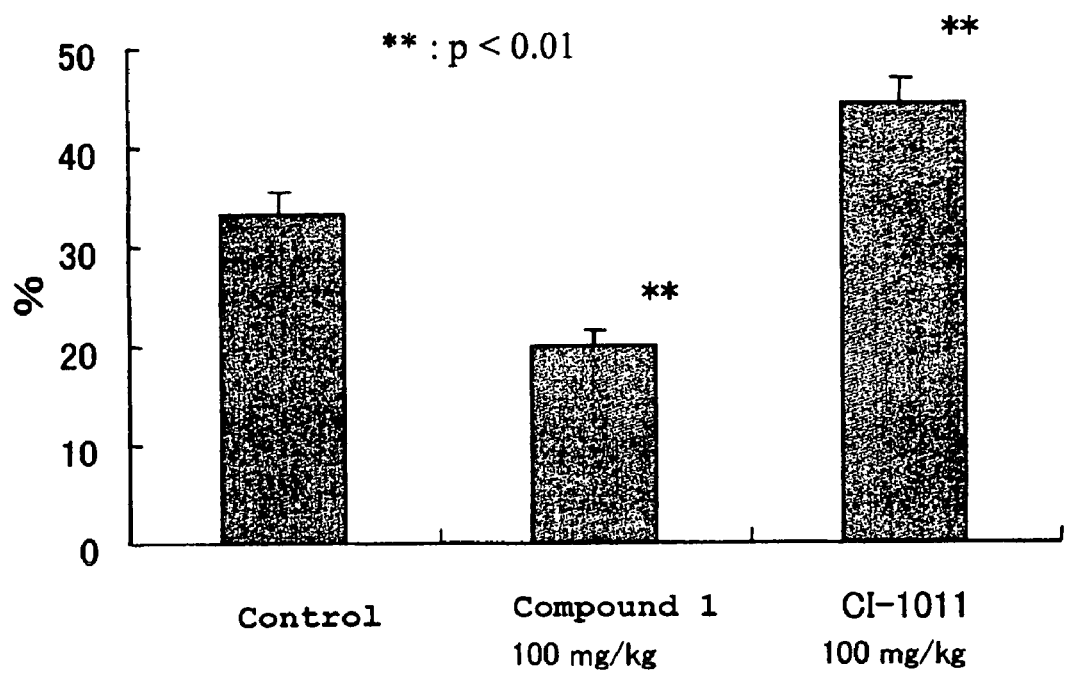
FIG. 6 shows the occupancy rate of macrophage obtained by the image analysis of immunohistochemical staining of macrophages in the specimens of surgically removed aortic sinus, after the compound 1 (100 mg/kg), CI-1011 (100 mg/kg) or vehicle were administered orally, twice a day for 12 weeks in male ApoE knockout mice.

Results of the occupancy rate of macrophage in the plaques calculated from the image analysis in FIG. 4 are shown in FIG. 6. The axis of ordinate in FIG. 6 indicates the occupancy rate (%) of the macrophage in the plaques. As shown in FIG. 6, the occupancy rate of the macrophage was significantly decreased in the compound 1 administered group as compared with the control group. Significant increase was observed in the CI-1011 administered group.

Figure 7:
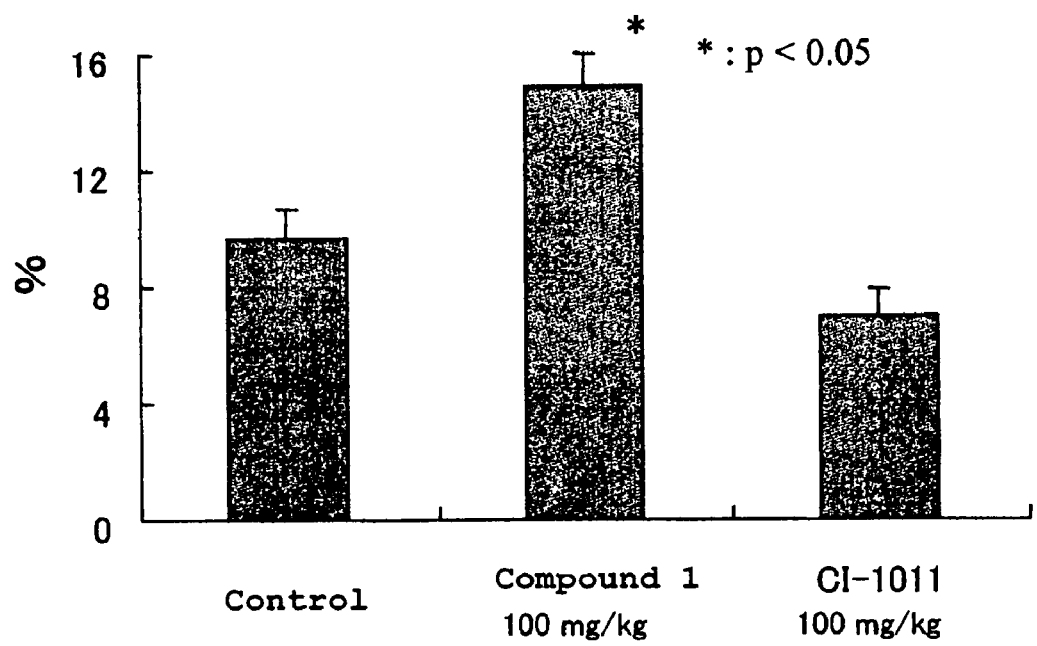
FIG. 7 shows the occupancy rate of collagen obtained by the image analysis of Sirius Red staining of macrophages in the specimens of surgically removed aortic sinus, after the compound 1 (100 mg/kg), CI-1011 (100 mg/kg) or vehicle were administered orally, twice a day for 12 weeks in male ApoE knockout mice.

Results of the occupancy rate of collagen in the plaques calculated from the image analysis in FIG. 5 are shown in FIG. 7. The axis of ordinate in FIG. 7 indicates the occupancy rate (%) of the collagen in the plaques. As shown in FIG. 7, the occupancy rate of the collagen was significantly increased in the compound 1 administered group as compared with the control group. On the other hand, decreasing tendency was observed in the CI-1011 administered group.

As described above, it was found that the compound 1 reduced the occupancy rate of macrophage in the plaques without making significant effect on changes of the plasma total cholesterol level, and increased the occupancy rate of collagen. In this way, the compound 1 increases collagen level, and simultaneously, reduces the occupancy rate of the macrophage to stabilize the plaques, thereby prevents rupture thereof.

Consequently, the present invention relates to a method of stabilizing lipid-rich plaques and a method of preventing the rupture thereof. More specifically, the present invention provides a method of stabilizing lipid-rich plaques and a method of preventing the rupture thereof, characterized in that an effective amount of the pharmaceutical composition containing the active ingredient consisting of one or more types of the compound 1, an acid salt thereof or a hydrate thereof is administered to a patient with lipid-rich plaques. Further, the present invention provides a pharmaceutical composition having activities for stabilizing lipid-rich plaques and preventing the rupture thereof comprising the active ingredient consisting of one or more types of the compound 1, an acid salt thereof or a hydrate thereof, and a pharmaceutically acceptable carrier thereof.

Since the compound 1, an acid salt thereof or a hydrate thereof of the present invention increases collagen in the lipid-rich plaques and reduces the occupancy rate of the macrophage, it can stabilize the lipid-rich plaques and prevents rupture thereof, thereby prevents thrombogenesis. Consequently, the present invention provides the preventive agents and/or therapeutic agents of various thrombus related diseases such as thrombosis caused by thrombogenesis, acute coronary syndrome, acute myocardial infarction, unstable angina, and peripheral artery obstruction, the pharmaceutical composition thereof, method for prevention and/or treatment using the same, and use for production thereof.

The pharmaceutical composition having stabilizing activity for plaques of the present invention comprises the compound 1 of the present invention as an active ingredient combined with a pharmaceutically acceptable carrier in the composition appropriate for administration form such as oral form or parenteral form, for example oral administration form, injectable form, suppository, ointment and patch, and can be produced by the formulation method known by the person skilled in the art. Also, in the present invention, an acid salt of the compound 1 or a hydrate of the compound 1 or an acid salt of the compound 1 can be used. The acid salt and the hydrate can be produced by the conventional method. Examples of acid for forming acid salt herein are inorganic acid such as hydrochloric acid, sulfuric acid, nitric acid, phosphoric acid, hydrobromic acid and hydroiodic acid, and organic acid such as acetic acid, lactic acid, succinic acid, tartaric acid, malic acid, maleic acid, fumaric acid, citric acid, ascorbic acid, methanesulfonic acid, besilate and toluenesulfonic acid. The compound 1, an acid salt thereof or a hydrate thereof can be used alone as an active ingredient, but can also be used in the mixture of two or more kinds as the active ingredient.

In the production of solid preparation for oral administration, for example, tablets, coated tablets, granules, powders and capsules can be produced by the conventional manner after diluent, if necessary, binder, disintegrator, lubricant, coloring agent, flavoring substance and corrigent are added to the compound 1, an acid salt thereof or a hydrate thereof. Examples of such additives can be the commonly used materials in the relevant field. For example, diluent include lactose, white soft sugar, sodium chloride, glucose, starch, calcium carbonate, kaolin, crystalline cellulose, silicic acid, etc.; binders include water, ethanol, propanol, simple syrup, glucose solution, starch suspension, gelatin solution, carboxymethyl cellulose, hydroxypropyl cellulose, hydroxypropyl starch, methylcellulose, ethylcellulose, shellac, calcium phosphate, polyvinylpyrrolidone, etc.; disintegrators include dry starch, sodium alginate, agar powder, sodium hydrogen carbonate, calcium carbonate, sodium lauryl sulfate, mono glyceride stearate, lactose, etc.; lubricants include purified talc, stearate, sodium borate, polyethylene glycol, etc.; and corrigents such as white soft sugar, bitter orange peel, citric acid, tartaric acid, etc.

In case of preparing liquids and solutions for oral administration, for example, the liquid preparation for oral administration, syrup, elixir, etc. can be produced in the conventional means by adding, if necessary, flavoring substance, buffer, stabilizing agent, corrigent, etc. to the above described compound 1, an acid salt thereof or a hydrate thereof. Examples of flavoring substances are as mentioned above, and those of buffers are sodium citrate, etc. and stabilizing agents are tragacanth, gum acacia, gelatin, etc.

In case of preparing injectable preparation, for example, the subcutaneous injection, intramuscular injection, intravenous injection, etc. can be produced in the conventional means by adding, if necessary, pH adjusting agent, buffer, stabilizing agent, tonicity adjusting agent, local anesthetic, etc. to the above described compound 1, an acid salt thereof or a hydrate thereof. Examples of the pH adjusting agent and buffer are sodium citrate, sodium acetate, sodium phosphate, etc. Examples of stabilizing agent are sodium pyrosulfite, EDTA, thioglycolic acid, thiolactic acid, etc. Examples of local anesthetics are procaine hydrochloride, lidocaine hydrochloride, etc. Examples of tonicity adjusting agents are sodium chloride, glucose, etc.

Other dosage forms can be produced according to the known methods. The thus obtained pharmaceutical composition having activity for stabilizing plaques of the present invention is effective for stabilizing the plaques in atherosclerotic lesions, prevention of thrombogenesis accompanied to rupture of plaques, prevention and/or treatment of acute coronary syndrome, prevention and/or treatment of acute myocardial infarction, prevention and/or treatment of unstable angina, and prevention and/or treatment of peripheral artery obstruction.

An applied dose of the pharmaceutical composition having activity for stabilizing plaques of the present invention depends on body weight, age, sex, symptoms of patients, dosage form and frequency of administration, and is preferably administered generally the compound 1, an acid salt thereof or a hydrate thereof, 0.01-1000 mg/day, preferably 0.1-100 mg/day, in adult, once or several times a day by oral or parenteral administration.

The contents described in U.S. Patent Application No. 60/498,610 are incorporated herein in the entirety thereof.

The present invention will be explained in detail by way of Examples hereinbelow, but the present invention is not limited thereto.

EXAMPLE 1

Anti-arterial sclerotic action of the drug was examined according to the method described herein below by using ApoE knockout mice with primary hyperlipidemia.

(1) Test Method

1. Test Animal

Home breeding male ApoE knockout mice, (C57BL/6J-ApoE<tmlUnc>, Jackson Labo™) were bred under common condition, 8 weeks old, were used for test.

2. Test Drug and Preparation of the Test Drug, and Method and Term of Administration The compound 1 (Example 32, WO 98/54153) and control drug, CI-1011 (Example 5, WO 94/26702), were synthesized according to methods described in each publication. The compound 1 and CI-1011 were dissolved (the compound 1) or suspended (CI-1011) in aqueous solution of 0.5% methylcellulose (MC). The solution or suspension was prepared to be a dose of 100 mg/kg and a volume for administration of 0.1 mL/10 g body weight. The control group (no drug administered group) received the solvent, aqueous solution of 0.5% methylcellulose (MC). Prepared drug solution and suspension were administered twice a day, orally, for continuing to 12 weeks (up to 20 weeks old) (total 3 groups, each 15 animal).

3. Observational and Inspection Method

A. Plasma Total Cholesterol Level

After ending the final administration, mice were fasted. In the next morning, mice were laparotomized under pentobarbital sodium anesthesia to expose abdominal vein and collected blood sample 1 mL. The collected blood was centrifuged at 3000 rpm for 15 minutes to collect the plasma. Plasma total cholesterol level was assayed by using cholesterol E-test Wako (cholesterol oxidase DAOS method).

B. Histological Evaluation

After collecting the blood, animals were undergone thoracotomy and 20-G injection needle was punctured into the cardiac apex. Physiological saline and subsequently 4% paraformaldehyde were perfused from the cardiac apex under the perfusion pressure at 120 cmH$_2$O for 5 minutes to fixate by perfusion. Heart and thoracic aorta were collected and fixated with the fixative by immersing for a day or more. Thereafter, aortic sinus was cut off and embedded in paraffin. Serial sections of specimens were prepared and stained with Victoria blue-hematoxylin and eosin staining, Azan staining, macrophage immunohistochemical staining (anti-CD11b antibody) and Sirius Red staining. Using the specimens of Victoria blue-hematoxylin and eosin staining, the internal elastic layer was specified by observation of optical microscope, and the cross-sectional area of the plaques was analyzed (Win ROOF, Mitsuya Shoji K.K.). Similarly, the area of macrophages was measured by using the specimens of macrophage immunohistochemical staining, and a ratio in total area of the plaques (the occupancy rate of macrophages) was calculated. Further, the area of collagen was measured by using Sirius Red staining, and a ratio occupied with collagen in total area of the plaques (the occupancy rate of collagen) was calculated.

4. Statistical Analysis and Data Processing

Obtained results are shown in mean±standard error. Test of significance between the control group and the drug-administered group is performed by Dunnett's test.

(2) Results

A. Plasma Total Cholesterol Level

Plasma total cholesterol level in each group is shown in FIG. 1. The plasma total cholesterol level in the control group is 641.8±23.0 mg/dL, whereas the plasma total cholesterol level in the compound 1, 100 mg/kg administered group is 535.0±22.8 mg/dL, and although it is significant (P<0.01), low decreasing effect is shown. The plasma total cholesterol level in the CI-1011, 100 mg/kg administered group is 360.3±19.4 mg/dL, and it is significant (P<0.01), and is characterized by a great lowering effect as compared with the compound 1. As the results of the above, tested drugs exhibit decreased action for plasma total cholesterol level, and the activity is found to exhibit remarkably in CI-1011, 100 mg/kg administered group.

B. Histological Evaluation

The cross-sectional area of the plaques measured by Victoria blue-hematoxylin and eosin staining in each group is shown in FIG. 2. The cross-sectional area of the plaques in the control group is 0.23±0.03 mm$^2$, whereas the cross-sectional area of the plaques in the compound 1, 100 mg/kg administered group, is 0.22±0.03 mm$^2$, consequently no difference was observed. Contrary to that, the cross-sectional area of the plaques in the CI-1011, 100 mg/kg administered group, is 0.09±0.01 mm$^2$, consequently reducing action for the cross-sectional area of the plaques is stronger than the compound 1 and is exhibited significantly (P<0.01). As the results of the above, the reducing action for the cross-sectional area of the plaques, namely the plaque reducing action is observed in the CI-1011, 100 mg/kg administered group.

Results of Azan staining, macrophage immunohistochemical staining and Sirius Red staining are shown in FIG. 3-FIG. 5. In each figure, the under side corresponds to the adventitia.

In the specimens of Azan staining (FIG. 3), the surface layer side of the intima consists largely of the pale red stained foamy macrophages, and the blue stained extracellular matrix was slightly observed in the deep layer. Large numbers of white defective acicular areas called cholesterol craft were observed. Contrary to that, although the cross-sectional area of the plaques in the compound 1, 100 mg/kg administered group was not so different as compared with the control group, the plaques consisted of small area of cellular components and large numbers of surrounding extracellular matrix. In CI-1011 administered group, although the cross-sectional area of the plaques was smaller as compared with that of the control group, the plaques consisted largely of red stained macrophage and the blue stained extracellular matrix was scanty.

Results of the macrophage immunohistochemical staining are shown in FIG. 4. As shown in FIG. 4, although the macrophages were abundantly observed specifically in the surface layer side in the control group, the macrophages were occasionally observed in the compound 1 administered group. Contrary to that, the macrophages were observed abundantly in whole plaques in the CI-1011 administered group.

Results of Sirius Red staining are shown in FIG. 5. As shown in FIG. 5, compactly arranged collagen fibers were observed in whole plaques in the compound 1 administered group as compared with the control group. However, in CI-1011 administered group, smaller numbers of collagen fibers were observed as compared with the control group.

Results of the occupancy rate of macrophage in the plaques calculated from the image analysis in FIG. 4 are shown in FIG. 6. As shown in FIG. 6, the occupancy rate of the macrophage was 33.2±2.2% in the control group, whereas the compound 1, 100 mg/kg administered group was significantly decreased to 20.0±1.7% (P<0.01). Contrary to that, it was significantly increased to 44.0±2.7% (P<0.01) in the CI-1011, 100 mg/kg administered group.

Results of the occupancy rate of collagen in the plaques calculated from the image analysis in FIG. 5 are shown in FIG. 7. As shown in FIG. 7, the occupancy rate of the collagen was 9.6±1.1% in the control group, whereas it was significantly increased to 14.9±1.0% in the compound 1, 100 mg/kg administered group (P<0.05). On the other hand, decreasing tendency was shown as 7.0±0.9% in the CI-1011, 100 mg/kg administered group.

As obvious from FIG. 6 and FIG. 7, the significant decrease of the occupancy rate of macrophage and the significant increase of the occupancy rate of collagen were observed in the compound 1, 100 mg/kg administered group as compared with the control group, whereas the significant increase of the occupancy rate of macrophage and decreased tendency of the occupancy rate of collagen were observed in the CI-1011, 100 mg/kg administered group. Namely, quite unexpectedly, even in the similar ACAT inhibitor, completely different action was confirmed against the plaques.

As explained hereinabove, effects of the compound 1 and CI-1011 having reducing activity for the plasma total cholesterol level based on ACAT inhibitory action were examined on the plasma total cholesterol level, the cross-sectional area of the plaques, and the histological evaluation. Results indicated that the CI-1011 exhibited decreasing effect on the cross-sectional area of the plaques, i.e. the plaque reducing action, at the concentration for decreasing the plasma total cholesterol level, but exhibited increase in the occupancy rate of the macrophage and decrease in the occupancy rate of the collagen, consequently it was demonstrated that the CI-1011 rather destabilized the plaques qualitatively. On the contrary, the compound 1 only slightly reduced the plasma total cholesterol level and exhibited no plaque reducing action, but exhibited decrease in the occupancy rate of the macrophage and increase in the occupancy rate of the collagen, consequently it was demonstrated that the compound 1 had remarkable plaque stabilizing action.

INDUSTRIAL APPLICABILITY

According to the present invention, a method of stabilizing lipid-rich plaques in atherosclerotic lesions and a method of preventing the rupture thereof can be provided. More specifically, a method of stabilizing lipid-rich plaques and a method of preventing the rupture thereof by suppressing accumulation of macrophages and increasing collagen in the plaque lesions by administering an effective amount of 2-[4-[2-(benzimidazol-2-ylthio)ethyl]piperazin-1-yl]-N-[2,4-bis(methylthio)-6-methyl-3-pyridyl]acetamide, an acid salt thereof or a hydrate thereof can be provided.

What is claimed is:

1. A method of stabilizing lipid-rich plaques, comprising administering a therapeutically effective amount of 2-[4-[2-(benzimidazol-2-ylthio)ethyl]piperazin-1-yl]-N-[2,4-bis(methylthio)-6-methyl-3-pyridyl]acetamide or an acid salt thereof or a hydrate thereof to a patient with lipid-rich plaques.

2. A method of treating thrombogenesis due to the rupture of lipid-rich plaques, comprising administering a therapeutically effective amount of 2-[4-[2-(benzimidazol-2-ylthio)ethyl]piperazin-1-yl]-N-[2,4-bis(methylthio)-6-methyl-3-pyridyl]acetamide or an acid salt thereof to a patient with lipid-rich plaques.

3. A method of treating acute coronary syndrome due to the rupture of lipid-rich plaques, comprising administering a therapeutically effective amount of 2-[4-[2-(benzimidazol-2-ylthio)ethyl]piperazin-1-yl]-N-[2,4-bis(methylthio)-6-methyl-3-pyridyl]acetamide or an acid salt thereof or a hydrate thereof to a patient with lipid-rich plaques.

4. A method of treating acute myocardial infarction due to the rupture of lipid-rich plaques, comprising administering a therapeutically effective amount of 2-[4-[2-(benzimidazol-2-ylthio)ethyl]piperazin-1-yl]-N-[2,4-bis(methylthio)-6-methyl-3-pyridyl]acetamide or an acid salt thereof to a patient with lipid-rich plaques.

5. A method of treating unstable angina due to the rupture of lipid-rich plaques, comprising administering a therapeutically effective amount of 2-[4-[2-(benzimidazol-2-ylthio)ethyl]piperazin-1-yl]-N-[2,4-bis(methylthio)-6-methyl-3-pyridyl]acetamide or an acid salt thereof to a patient with lipid-rich plaques.

6. A method of treating peripheral artery obstruction due to the rupture of lipid-rich plaques, comprising administering a therapeutically effective amount of 2-[4-[2-(benzimidazol-2-ylthio)ethyl]piperazin-1-yl]-N-[2,4-bis(methylthio)-6-methyl-3-pyridyl]acetamide or an acid salt thereof to a patient with lipid-rich plaques.

7. The method of claim 1, wherein said patient has acute coronary syndrome.

8. The method of claim 1, wherein said patient has acute myocardial infarction.

9. The method of claim 1, wherein said patient has unstable angina.

10. The method of claim 1, wherein said patient has peripheral artery obstruction.

* * * * *